United States Patent
Bontus et al.

(10) Patent No.: US 7,187,747 B2
(45) Date of Patent: Mar. 6, 2007

(54) COMPUTERIZED TOMOGRAPHY METHOD WITH HELICAL RELATIVE MOVEMENT AND CONICAL BEAM

(75) Inventors: Claas Bontus, Hamburg (DE); Thomas Koehler, Norderstedt (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 84 days.

(21) Appl. No.: 10/546,231

(22) PCT Filed: Feb. 11, 2004

(86) PCT No.: PCT/IB2004/000346

§ 371 (c)(1),
(2), (4) Date: Aug. 18, 2005

(87) PCT Pub. No.: WO2004/075106

PCT Pub. Date: Sep. 2, 2004

(65) Prior Publication Data

US 2006/0233294 A1 Oct. 19, 2006

(30) Foreign Application Priority Data

Feb. 19, 2003 (EP) .................................. 03100384

(51) Int. Cl.
*H05G 1/60* (2006.01)

(52) U.S. Cl. ............................................. 378/15; 378/4
(58) Field of Classification Search .............. 378/4–20, 378/901

See application file for complete search history.

(56) References Cited

U.S. PATENT DOCUMENTS

| 5,270,923 A | 12/1993 | King et al. ................. 382/131 |
| 5,515,409 A | 5/1996 | Hsieh .......................... 378/15 |
| 5,974,110 A | 10/1999 | Hu ............................... 378/19 |
| 6,108,575 A | 8/2000 | Besson ....................... 600/425 |
| 6,275,561 B1* | 8/2001 | Danielsson ................. 378/15 |
| 2006/0140335 A1* | 6/2006 | Heuscher et al. .............. 378/4 |

FOREIGN PATENT DOCUMENTS

WO WO 02/30282 A2 4/2002

OTHER PUBLICATIONS

Katsevich, A.; Analysis of an exact inversion algorithm for spiral cone-beam CT; 2002; Phys. in Med. & Biol.; 47:2583-2597.
Katsevich, A.; Theoretically Exact Filtered Backprojection-type Inversion Algorithm for Spiral CT; 2002; SIAM J. Appl. Math; 62:6:2012-2026.
Kohler, T., et al.; Evaluation of Helical Cone-Beam CT Reconstruction Algorithms; 2003; IEEE; pp. 1217-1220.
Proksa, R., et al.; The n-Pl-Method for Helical Cone-Beam CT; 2000; IEEE; 19:9:848-863.

* cited by examiner

*Primary Examiner*—Courtney Thomas
*Assistant Examiner*—Alexander Taningco
(74) *Attorney, Agent, or Firm*—Thomas M. Lundin

(57) ABSTRACT

The invention relates to a computerized tomography method, in which an examination area is scanned radiographically along a helical trajectory by a conical beam. The radiation transmitted through the examination area is measured by means of a detector unit, wherein the absorption distribution in the examination area is reconstructed exactly or at least quasi-exactly from these measured values. Reconstruction uses redundant measured values and comprises derivation of the measured values from parallel rays of different projections, integration of these values along κ-lines, weighting of these values and back-projection.

9 Claims, 10 Drawing Sheets

COMPUTERIZED TOMOGRAPHY METHOD WITH HELICAL RELATIVE MOVEMENT AND CONICAL BEAM

Figure 1:
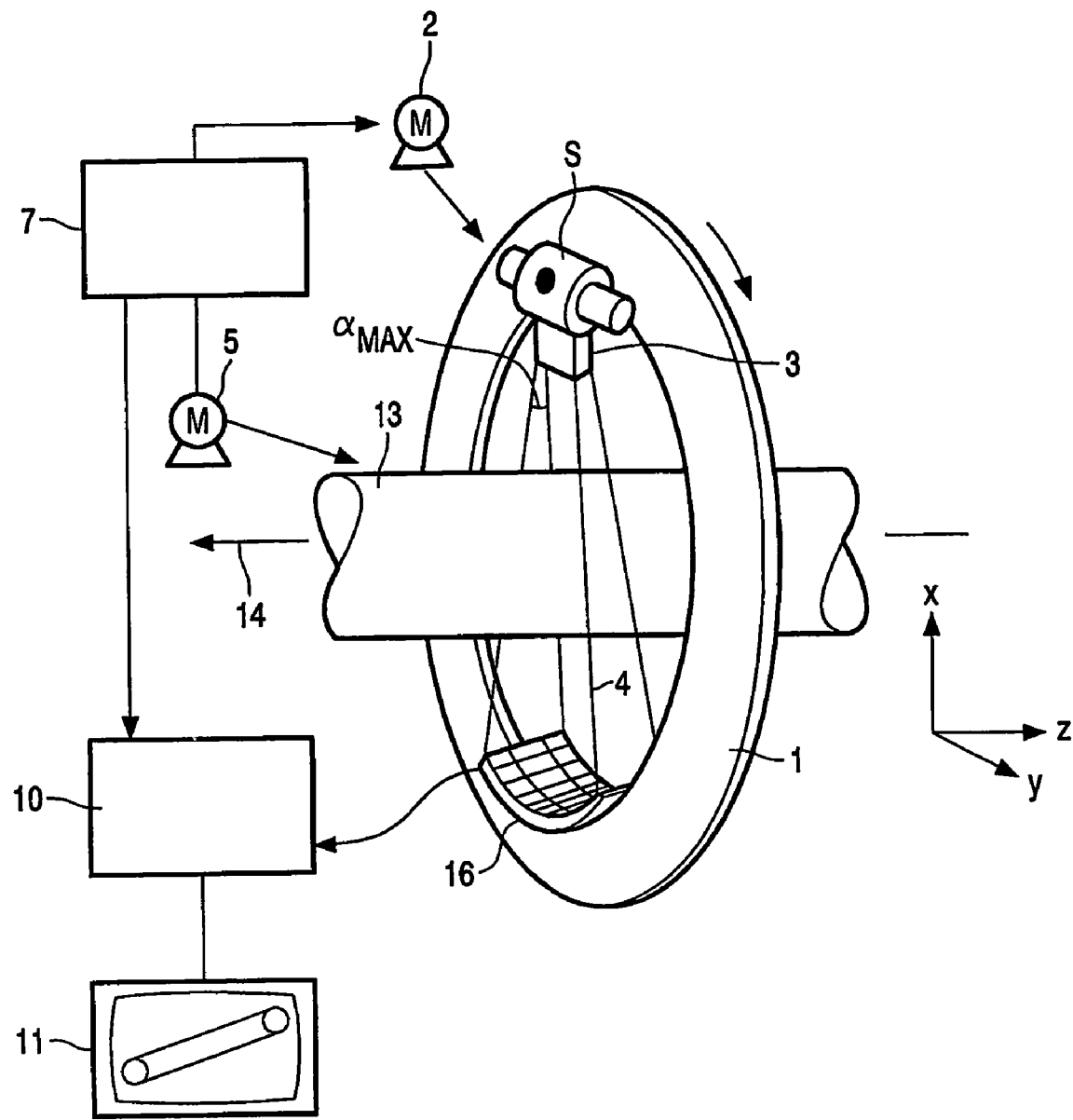

The invention relates to a computerized tomography method, in which an examination area is scanned radiographically along a helical trajectory by a conical beam. In addition, the invention relates to a computer tomograph and to a computer program for controlling the computer tomograph.

In known methods of the above-mentioned type, the spatial profile of the absorption or of the attenuation of the radiation in the examination area may be reconstructed from the measured values acquired by a detector unit. Exact reconstruction methods may be used in this respect, which are customarily based on radon inversion. These reconstruction methods based on radon inversion require high computing power and lead to discretization errors in the reconstructed images.

A further exact reconstruction method, which requires less computing power than the above-mentioned method and leads to fewer discretization errors, is known from "Analysis of an Exact Inversion Algorithm for Spiral Cone-Beam CT", Physics Medicine and Biology, vol. 47, pp. 2583–2597 (E1). This method is based on filtered back-projection and uses measured values which have been detected using so-called PI-acquisition. In PI-acquisition, the radiation source is moved on the helical trajectory in such a way that each location to be reconstructed within the examination area is illuminated over an angular range of 180°. If such a location is illuminated over an angular range greater than 180°, the surplus, redundant measured values are not taken into account in reconstruction. This results in a poor signal-to-noise ratio. Moreover, PI-acquisition limits the distance between two adjacent turns of the helical trajectory. With too small a distance, more measured values are acquired than are necessary. This exposes a patient to unnecessarily large amounts of radiation during an examination. On the other hand, if the distance is too large, not every location to be reconstructed in the examination area is illuminated over an angular range of 180°. Variation of the distance between two adjacent turns of the helix is thus difficult to achieve, although it is frequently necessary in particular in medical examinations.

It is therefore an object of the present invention to provide a method which allows exact or at least quasi-exact reconstruction of the absorption distribution in the examination area with the aid of filtered back-projection without the above-mentioned disadvantages. The term "quasi-exact" will be explained below in connection with equation (24).

This object is achieved according to the invention by a computerized tomography method having the steps:

a) generation with a radiation source of a conical beam passing through an examination area and an object located therein, b) production of relative movement between the radiation source on the one hand and the examination area on the other, which comprises rotation about an axis of rotation and displacement parallel to the axis of rotation and takes the form of a helix, wherein the position of the radiation source on the helix is defined by an angular position, c) acquisition of measured values with a detector unit during the relative movement, whereby the measured values depend on the intensity in the beam on the other side of the examination area, and the detector unit (16) comprises a detector surface, d) reconstruction of a CT image of the examination area from the measured values, wherein an exact or quasi-exact, filtered 3D back-projection with redundant measured values is performed according to the following steps:

determination of the partial derivative of measured values from parallel rays with different radiation source positions depending on the angular position of the radiation source on the helix, filtering of the derived measured values along filter lines, wherein a plurality of filter lines are assigned to at least some of the measured values, such that these measured values are filtered several times, reconstruction of the absorption distribution at locations to be reconstructed in the examination area by back-projection of the measured values.

In contrast to known exact methods, which use filtered 3D back-projection, in the case of the invention redundant measured values are also used for reconstruction. This results in a better signal-to-noise ratio in the reconstructed CT image. In addition, the use of redundant data allows a reduction in the distance between two adjacent turns of the helical trajectory while exposing a patient to be examined to the same or at least an only slightly higher level of radiation, since the larger signal-to-noise ratio permits the use of a smaller dose of radiation while maintaining the same quality of CT image.

Claims 2, 4, 5 and 6 describe preferred types of measured value filtering, wherein the measured values are multiplied with a weighting factor, which corresponds to the reciprocal of the sine of the κ-angle, i.e. they may be multiplied with the reciprocal of the sine of the κ angle or with an approximation of this weighting factor. The approximation may be produced by the Taylor development for example or other known methods. This multiplication of the measured values with the weighting factor results in high quality reconstructed images.

Claim 3 discloses a preferred method of determining filter lines, which leads to good reconstruction results.

Claim 7 describes a preferred method in which the measured values are multiplied with a further weighting factor immediately prior to back-projection. This leads to a further improvement in image quality.

A computer tomograph for performing the method according to the invention is described in claim 8. Claim 9 defines a computer program for controlling a computer tomograph as claimed in claim 8.

Figure 2:
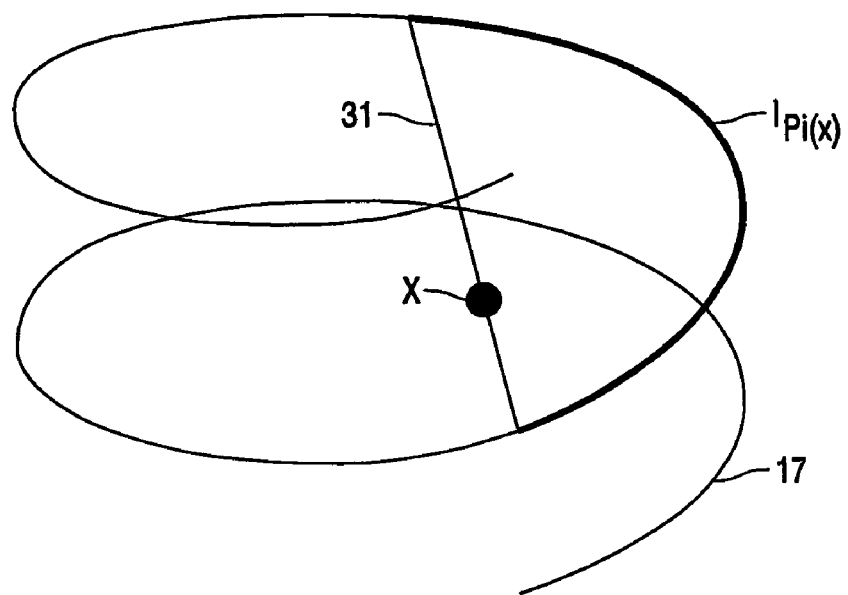
Figure 3:
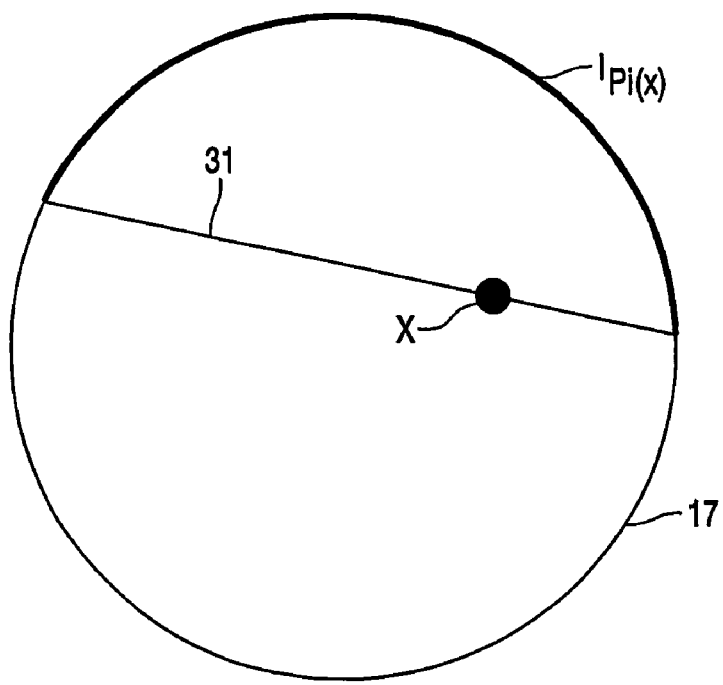
Figure 4:
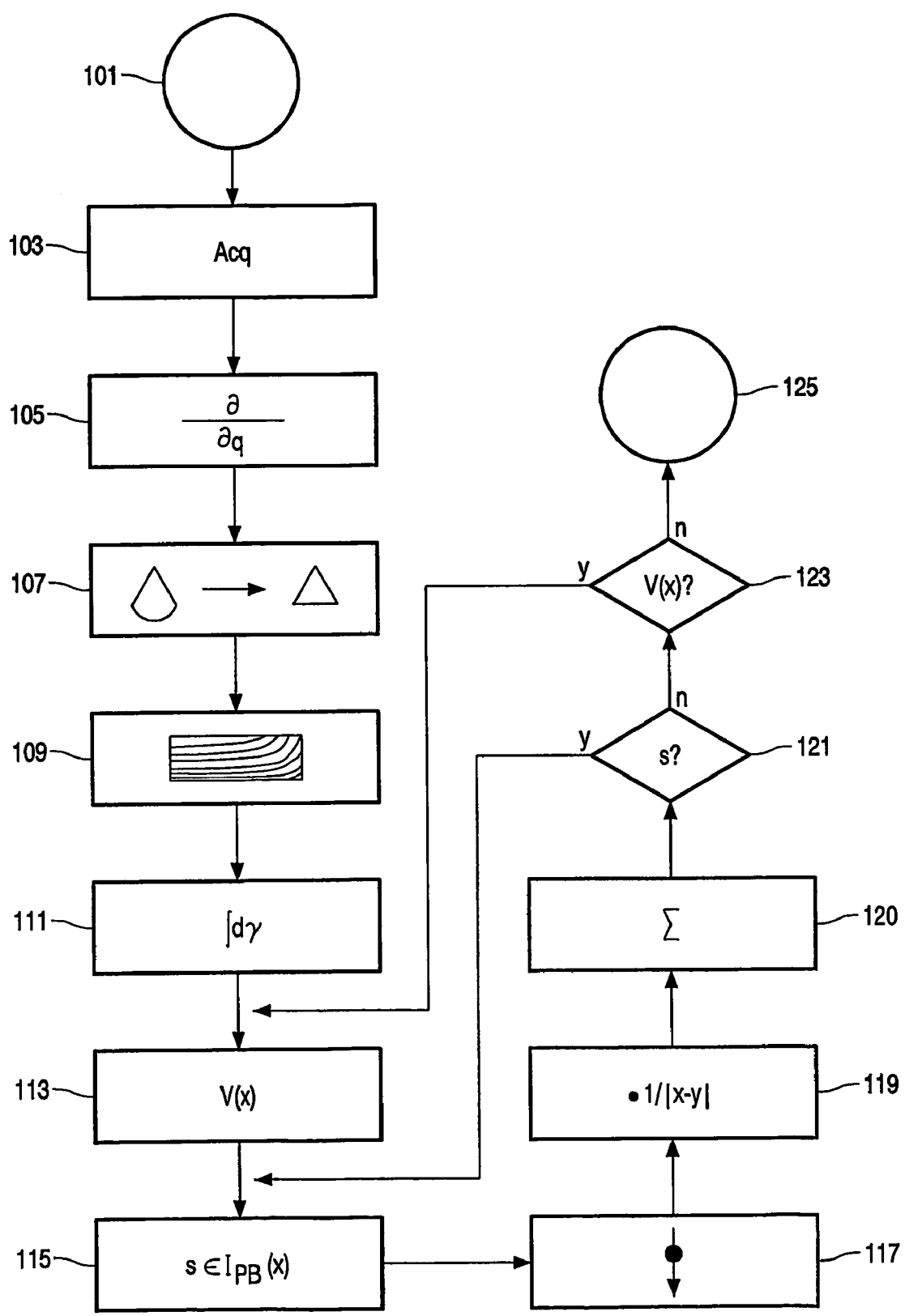
Figure 5:
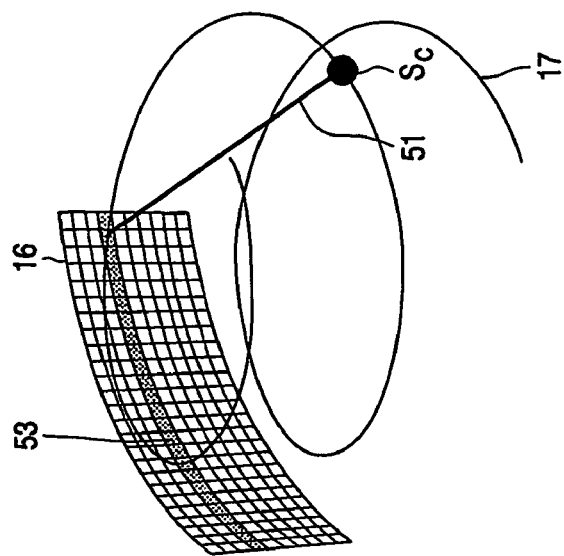
Figure 5:
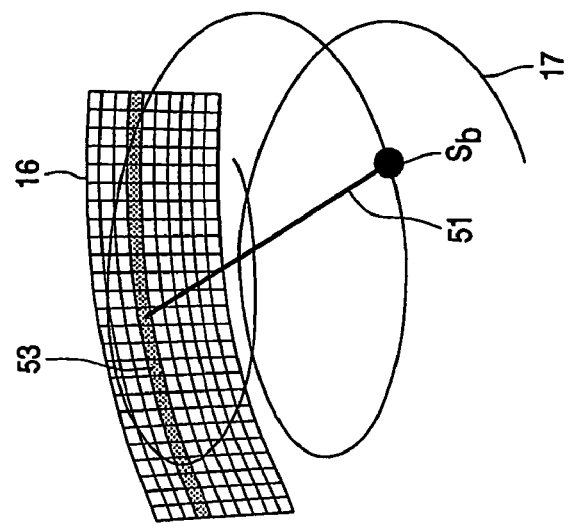
Figure 5:
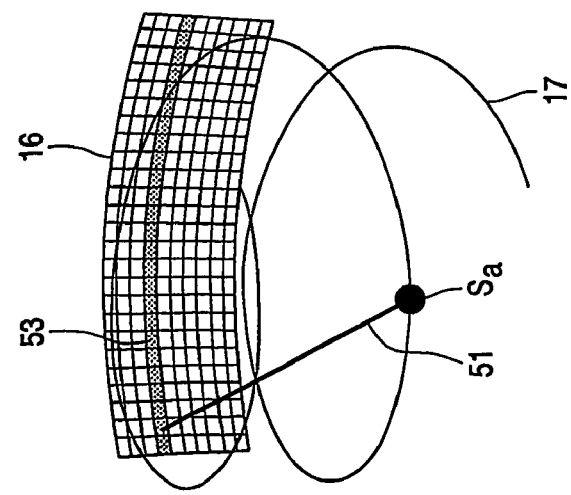
Figure 6:
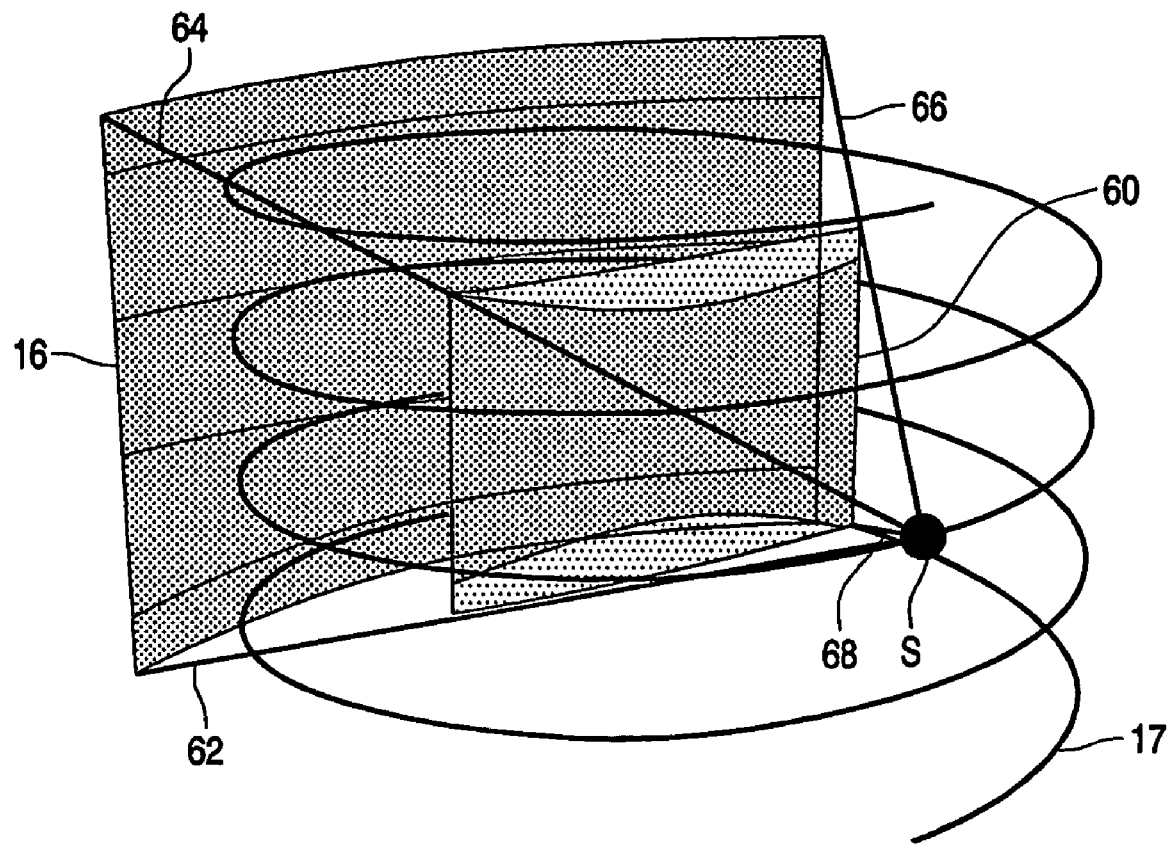
Figure 7:
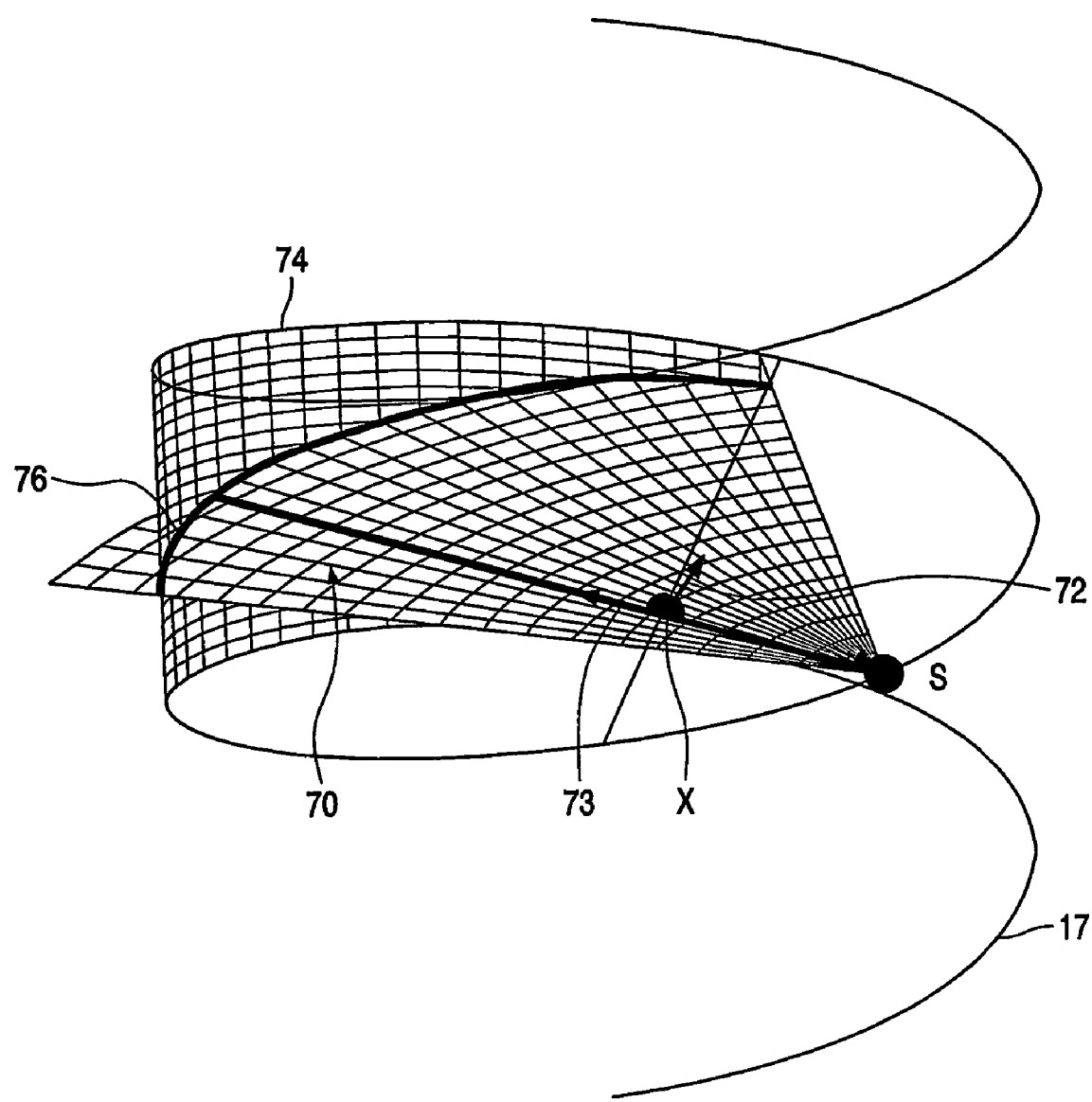
Figure 8:
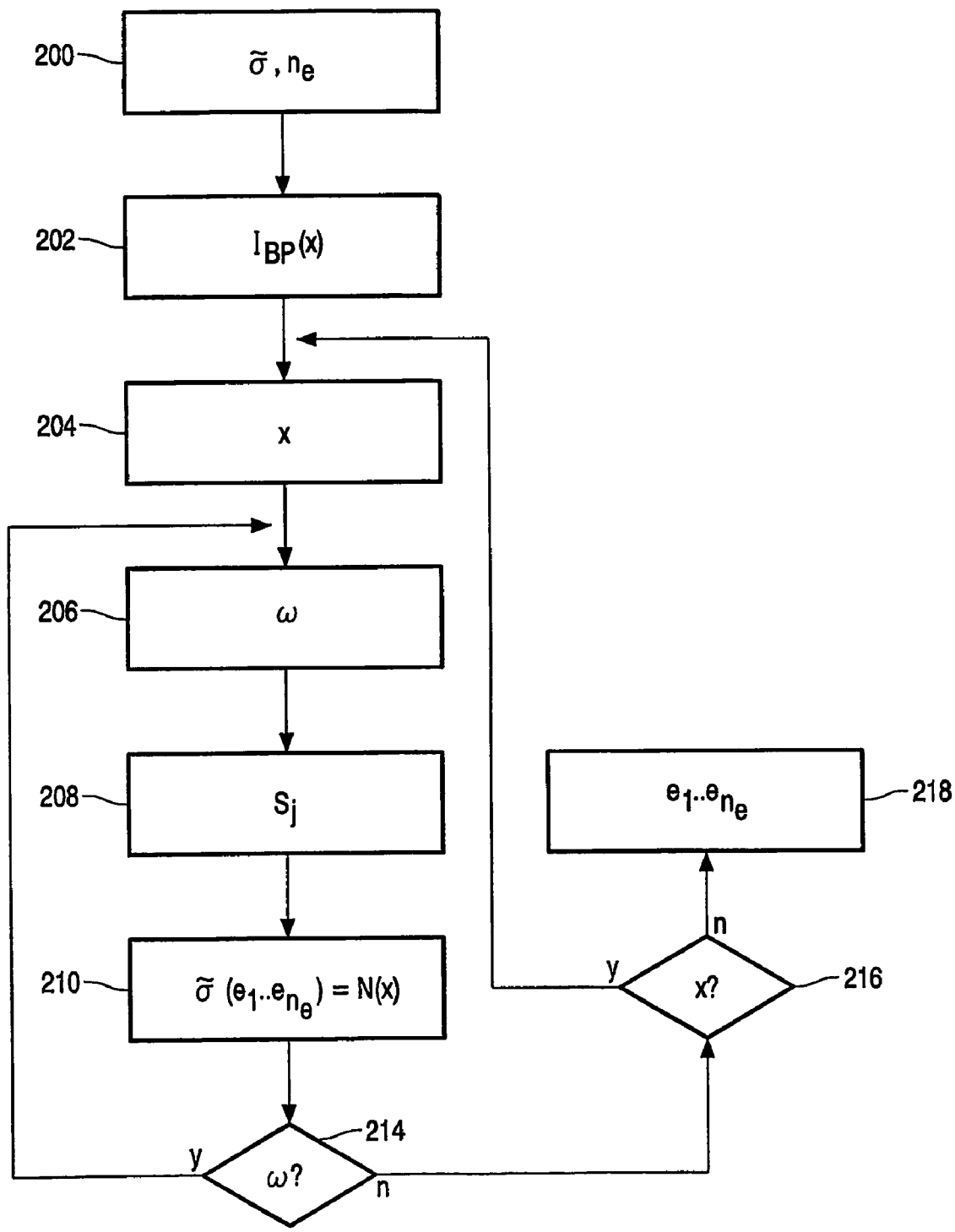

The invention will be further described with reference to examples of embodiment shown in the drawings to which, however, the invention is not restricted. In the Figures:

FIG. 1 shows a computer tomograph, with which the method according to the invention may be performed, FIG. 2 shows a PI-boundary line and an area of a helical trajectory, from which a location within the examination area is illuminated, FIG. 3 shows the PI-boundary line and the area of the trajectory, from which a location within the examination area is illuminated, projected onto a plane which is oriented perpendicularly to the axis of rotation, FIG. 4 is a flow chart of the method according to the invention, FIG. 5 is a perspective view of parallel rays from different radiation source positions, which hit a detector row, FIG. 6 is a perspective view of a helical trajectory and a focus-centered and a planar detector, FIG. 7 is a perspective view of a helical trajectory, a detector, a κ-plane and a filter line, FIG. 8 is a flow chart for determining κ-vectors suitable for reconstruction, and FIG. 9 to FIG. 13 show filter lines and filter directions on the planar detector.

The computer tomograph illustrated in FIG. 1 comprises a gantry 1, which may rotate about an axis of rotation 14 extending parallel to the z direction of the system of coordinates illustrated in FIG. 1. To this end, the gantry 1 is driven by a motor 2 at a preferably constant but adjustable angular velocity. A radiation source S, for example an X-ray tube, is attached to the gantry 1. This is provided with a collimator arrangement 3, which extracts a conical beam 4 from the radiation generated by the radiation source S, i.e. a beam which has a finite extension other than zero both in the z direction and in a direction perpendicular thereto (i.e. in a plane perpendicular to the axis of rotation).

The beam 4 penetrates a cylindrical examination area 13, in which there may be located an object, e.g. a patient on a patient support table (neither of which is shown) or indeed a technical object. After passing through the examination area 13, the beam 4 hits a detector unit 16 with detector surface attached to the gantry 1, which surface comprises a plurality of detector elements, which are arranged in this embodiment in a matrix of rows and columns. The detector columns extend parallel to the axis of rotation 14. The detector rows are located in planes perpendicular to the axis of rotation, in this embodiment on a circular arc about the radiation source S (focus-centered detector). In other embodiments, however, they may also take other forms, e.g. they may describe a circular arc about the axis of rotation 14 or be rectilinear. Each detector element hit by the beam 4 supplies a measured value for a ray from the beam 4 in each position of the radiation source.

The aperture angle of the beam 4 designated $\alpha_{max}$ determines the diameter of the object cylinder within which the object to be examined is located during acquisition of the measured values. The aperture angle is defined as the angle which a ray lying in a plane perpendicular to the axis of rotation 14 at the edge of the beam 4 forms with a plane defined by the radiation source S and the axis of rotation 14. The examination area 13 or the object or the patient support table may be displaced by means of a motor 5 parallel to the axis of rotation 14 or the z axis. However, as an equivalent thereto, the gantry could also be displaced in this direction. If the object is a technical object and not a patient, the object may be rotated during examination, while the radiation source S and the detector unit 16 stand still.

If the motors 2 and 5 run simultaneously, the radiation source S and detector unit 16 describe a helical trajectory relative to the examination area 13. If, on the other hand, the motor 5 for feed in the direction of the axis of rotation 14 stands still and the motor 2 causes the gantry to rotate, a circular trajectory is obtained for the radiation source S and the detector unit 16 relative to the examination area 13. Only the helical trajectory will be considered below.

The measured values acquired by the detector unit 16 are fed to an image processing computer 10, which is connected to the detector unit 16, e.g. by means of contactlessly operating data transmission (not shown). The image processing computer 10 reconstructs the absorption distribution in the examination area 13 and displays it, for example on a monitor 11. The two motors 2 and 5, the image processing computer 10, the radiation source S and transfer of the measured values from the detector unit 16 to the image processing computer 10 are controlled by a control unit 7.

In other embodiments, the acquired measured values may be fed for reconstruction firstly to one or more reconstruction computers, which forward the reconstructed data for example via a fiber-optic cable to the image processing computer.

Before the sequence of an embodiment of a measuring and reconstruction method which may be performed with the computer tomograph according to FIG. 1 is presented, the exact or quasi-exact back-projection of measured values will be described mathematically to assist in understanding.

During data acquisition, the radiation source moves along a helical trajectory. The position of the radiation source y(s) on this trajectory may be represented by $$y(s) = \begin{pmatrix} R\cos s \\ R\sin s \\ s\frac{h}{2\pi} \end{pmatrix} \quad (1)$$

wherein s denotes the angular position on the helix relative to any desired, but fixed reference angular position, R denotes the distance between the radiation source S and the axis of rotation 14 and h denotes the pitch. The pitch is defined here as the spacing between two adjacent turns of the helical trajectory, i.e. for example as table feed per rotation of the radiation source.

For each radiation source position y(s), the measured value corresponds to a line integral through an object function $f(x)$. Here, the object function denotes the absorption value at the location x in the examination area The line integral may be described by the following equation:

$$D_f(y(s), \Theta) = \int_0^\infty dl f(y + l\Theta), \quad (2)$$

wherein Θ is a unit vector, which distinguishes between measured values which, though caused by rays starting from the same radiation source position, hit different detector elements. The unit vector T thus indicates the direction of the ray associated with the measured value.

The purpose of all reconstruction methods is to obtain the object function $D_f(y(s),\Theta)$ from the measured values $f(x)$.

For PI-acquisition, a mathematically exact formula for reconstruction of the object function by filtered back-projection is known from E1:

$$f(x) = -\frac{1}{2\pi^2} \int_{I_{PI(x)}} ds \frac{1}{|x - y(s)|} \int_{-\pi}^{\pi} \frac{d\gamma}{\sin\gamma} \frac{\partial}{\partial q} D_f(y(q), \Theta(s, x, \gamma)) \bigg|_{q=s} \quad (3)$$

With reference to FIG. 2 and FIG. 3, $I_{PI}(x)$ denotes part of the helical trajectory which is enclosed by a PI-boundary line 31. The PI-boundary line 31 of a location x in the examination area and the helix portion $I_{PI}(x)$ are explained below. The radiation source S moves relative to the examination area on a helical trajectory 17 about a location x. The PI-boundary line 31 is the line which intersects the trajectory 17 at two points and the location x, wherein the helix portion $I_{PI}(x)$ enclosed by the line covers an angle smaller than $2\pi$.

The pitch established by the PI-acquisition may be defined with the assistance of the helix portion $I_{PI}(x)$. During PI-acquisition, the pitch should be selected in such a way that the radiation source is seen along the corresponding portion x of the helix from each location $I_{PI}(x)$ to be reconstructed in the examination area.

The direction of the rays T depends in equation (3) on the angular position s, the location x to be reconstructed in the examination area and the integration variable γ, hereinafter designated κ-angle, and may be expressed as follows $$\Theta(s,x,\gamma) = \cos\gamma \cdot \beta(s,x) + \sin\gamma \cdot e(s,x). \tag{4}$$

Here β(s,x) is a unit vector, which points from the radiation source position to the location to be reconstructed in the examination area:

$$\beta(s,x) = \frac{x - y(s)}{|x - y(s)|}. \tag{5}$$

Furthermore, the unit vector e(s,x) is oriented perpendicularly to β(s,x) and lies in the so-called κ-plane. It is designated the κ-vector and may be represented with the assistance of the normal vector u(s,x) of the κ-plane:

$$e(s,x) = \beta(s,x) \times u(s,x). \tag{6}$$

The surface normal u(s,x) and thus the κ-plane are given by the following equation:

$$(x - y(s)) \cdot u(s, s_2) = 0, \quad s_2 \in I_{PI}(x), \tag{7}$$

wherein $$u(s, s_2) = \tag{8}$$

$$\begin{cases} \frac{[y(s_1(s, s_2)) - y(s)] \times [y(s_2) - y(s)]}{|[y(s_1(s, s_2)) - y(s)] \times [y(s_2) - y(s)]|} \cdot sgn(s_2 - s), & 0 < |s_2 - s| < 2\pi \\ \frac{\dot{y}(s) \times \ddot{y}(s)}{|\dot{y}(s) \times \ddot{y}(s)|}, & s_2 = s \end{cases}$$

and $$s_1(s, s_2) = \begin{cases} \psi(s_2 - s) + s, & s \leq s_2 < s + 2\pi \\ \psi(s - s_2) + s_2, & s - 2\pi < s_2 < s \end{cases}. \tag{9}$$

Here, ψ is a function which fulfills the following relationship:

$$\psi(0) = 0, \; 0 < \psi'(t) < 1, \; t \in [0, 2\pi]. \tag{10}$$

The vectors $\dot{y}(s)$ and $\ddot{y}(s)$ denote the first and second derivatives of the radiation source position y(s) in accordance with the angular position s.

A detailed explanation of the above-stated equations may be found in publication E1, to which reference is hereby made.

A disadvantage of reconstruction according to equation (3) is that back-projection, i.e. integration via the angular positions s, is restricted to measured values whose radiation source positions lie in the interval $I_{PI}(x)$. Measured values which were acquired outside this portion of the helical trajectory 17 (redundant data) are not taken into account. Therefore, equation (3) is modified below in such a way that redundant measured values may also be used for reconstruction.

First of all, the object function ƒ(x) is represented by means of its Fourier transforms Fƒ(ξ):

$$f(x) = \int d^3\xi e^{2\pi i \xi \cdot x} Ff(\xi). \tag{11}$$

Then equation (2) is inserted into equation (3), wherein the object function is replaced by its Fourier representation according to equation (11) and the integration variables l and γ are transformed in accordance with $$u_1 = l\cos\gamma, \; u_2 = l\sin\gamma \tag{12}$$

This results in $$f(x) = \tag{13}$$

$$\int_{I_{PI}(x)} ds \int d^3\xi e^{2\pi i \xi \cdot y(s)} (\xi \cdot \dot{y}(s)) sgn(\xi \cdot e(s,x)) \delta(\xi \cdot (x - y(s))) Ff(\xi).$$

The vector ξ is represented below in spherical coordinates:

$$\xi = \xi\omega(\theta, \phi), \; \omega(\theta, \phi) = \begin{pmatrix} \sin\theta\cos\phi \\ \sin\theta\sin\phi \\ \cos\theta \end{pmatrix}. \tag{14}$$

In addition, the Fourier slice theorem is known from "The Mathematics of Computerized Tomography", F. Natterer, Wiley, New York, USA, 1986:

$$FRf(\xi, \omega) = Ff(\xi\sin\theta\cos\phi, \xi\sin\theta\sin\phi, \xi\cos\theta). \tag{15}$$

Here, Rƒ(ρ,ω) is the radon transform of the object function ƒ(x) and FRƒ(ξ,ω) is the Fourier transform of the radon transforms. They are stated by the following expressions:

$$Rf(\rho, \omega) = \int d^3x f(x) \delta(\rho - \omega \cdot x) \text{ and} \tag{16}$$

$$FRf(\xi, \omega) = \int_{-\infty}^{\infty} d\rho e^{-2\pi i \rho \xi} Rf(\rho, \omega). \tag{17}$$

Finally, the insertion of equation (15) into equation (13) using the symmetry relationship FRƒ(ξ,ω)=FRƒ(-ξ,-ω) results in $$f(x) = -\frac{1}{8\pi^2} \int_0^\pi d\theta \int_0^{2\pi} d\phi \sin\theta \sigma(x, \omega) R''f(\omega \cdot x, \omega). \tag{18}$$

Here, R"ƒ(ρ,ω) is the second derivative according to ρ of the radon transforms of the object function, and σ(x,ω) represents the following sum:

$$\sigma(x, \omega) = \sum_j sgn(\omega \cdot \dot{y}(s_j)) \cdot sgn(\omega \cdot e(s_j, x)), \; s_j \in I_{PI}(x). \tag{19}$$

The variables $s_j = s_j(x,\omega)$ denote those angular positions for which the equation $$(x - y(s_j)) \cdot \omega = 0 \tag{20}$$

is fulfilled.

E1 has now shown that for PI-acquisition and for the vectors e(s,x) defined in equations (6) to (10)

$$\sigma(x,\omega) = 1 \tag{21}$$

applies.

Hitherto, all the equations related to PI-acquisition. In particular, it is clear from equation (3), as already mentioned above, that the actual back-projection, i.e. the integration via the angular position s, is limited to the PI-interval $I_{PI}(x)$. Below, equation (3) is modified in such a way that integration via the angular positions s may be performed over any desired interval $I_{BP}(x)$ of the helical trajectory. The interval $I_{BP}(x)$ should then cover a range of the trajectory which is greater than $I_{Pl}(x)$, i.e. $I_{Pl}(x) \subseteq I_{BP}(x)$. Such a modification to equation (3) allows redundant measured values, i.e. measured values during whose acquisition the radiation source was not located in the interval $I_{Pl}(x)$ but rather in the interval $I_{BP}(X)$, to be taken into account during reconstruction of an object point $f(x)$.

Modification of the integration interval from $I_{Pl}(x)$ to $I_{BP}(x)$ leads in equation (18) merely to a modification of the function $\sigma(x,\omega)$ according to the following equation:

$$\sigma(x, \omega) = \sum_j sgn(\omega \cdot \dot{y}(s_j)) \cdot sgn(\omega \cdot e(s_j, x)), \, s_j \in I_{BP}(x). \quad (22)$$

Since the interval $I_{BP}(x)$ is larger than the interval $I_{Pl}(x)$, more angular positions $s_j$ could fill equation (20), such that $\sigma(x,\omega)$ would no longer be constant. However, for reconstruction according to equation (18), this is a prerequisite, as is clear above from equation (21).

Therefore, a new function $$\tilde{\sigma}(x, \omega) = \sum_j sgn(\omega \cdot \dot{y}(s_j)) \begin{bmatrix} sgn(\omega \cdot e_1(s_j, x)) + \ldots + \\ sgn(\omega \cdot e_{n_e}(s_j, x)) \end{bmatrix}, \, s_j \in I_{BP}(x) \quad (23)$$

is defined with new vectors, κ-vectors $e_k(s_j,x)$, $k=1, \ldots, n_e$, wherein the new vectors $e_k(s_j,x)$ are selected such that the function $\tilde{\sigma}(x,\omega)$ delivers a value which is independent of $\omega$ but may be dependent on x:

$$\tilde{\sigma}=N(x). \quad (24)$$

With such a choice of vectors, $\sigma(x,\omega))$ may be replaced by $\tilde{\sigma}/N(x)$ in equation (18), without equation (18) losing its exactness.

Once $\sigma(x,\omega)$ has been replaced by $\tilde{\sigma}/N(x)$ in equation (18), repetition of the arithmetic steps which led to equation (18) leads in reverse sequence to the following equation:

$$f(x) = \frac{1}{2\pi^2} \frac{1}{N(x)} \int_{I_{BP}(x)} ds \frac{1}{|x - y(s)|} \int_{-\pi}^{\pi} \frac{d\gamma}{\sin\gamma} \frac{\partial}{\partial q} \quad (25)$$

$$\left[ D_f \begin{matrix} (y(q), \Theta_1(s, x, \gamma)) + \ldots + \\ D_f(y(q), \Theta_{n_e}(s, x, \gamma)) \end{matrix} \right]\Big|_{q=s},$$

wherein $$\Theta_k(s, x, \gamma) = \cos\gamma \cdot \beta(s, x) + \sin\gamma \cdot e_k(s, x), \, k = 1, \ldots, n_e \quad (26)$$

applies.

In contrast to the known exact, filtered back-projection according to equation (3), back-projection, i.e. integration via the angular positions s, takes place according to equation (25) over the interval $I_{BP}(x)$. Consequently, redundant measured values are also back-projected.

According to the invention, the κ-vectors $e_k(s,x)$ are so selected that equation (24) is fulfilled in the case of given interval $I_{BP}(x)$ for all or at least for the majority of possible combinations of vectors $\omega$ and locations x in the examination area. If equation (24) is fulfilled for all possible combinations, equation (18) applies exactly, even after $\sigma(x,\omega)$ has been replaced by $\tilde{\sigma}/N(x)$. Therefore, back-projection according to equation (25) is in this case designated "exact". If, on the other hand, equation (24) is only fulfilled for a majority of the combinations, the filtered back-projection according to equation (25) is designated "quasi-exact" for the purposes of the invention. The filtered back-projection is thus quasi-exact, if equation (24) is fulfilled for more than 50% of the combinations of vectors $\omega$ and locations x in the examination area, i.e. for example for 60%, 70%, 80% or 90% of these combinations.

This mathematical description of exact reconstruction is now followed by a description of the sequence of an embodiment of a measuring and reconstruction method which may be performed with the computer tomograph of FIG. 1. Here, equation (25) is a standard specification with which the following steps according to the invention comply. The individual steps of the measuring and reconstruction method are shown in FIG. 4.

After initialization in step 101, the gantry rotates with an angular velocity which is constant in this example of embodiment. However, it may also vary, e.g. as a function of time or of radiation source position.

In step 103, the examination area or the object or the patient support table is displaced parallel to the axis of rotation and the radiation of the radiation source S is switched on, such that the detector unit 16 may detect the radiation from a plurality of angular positions. In this example of embodiment the pitch is selected in such a way that, from each location x in the examination area, the radiation source S is visible over an angular range of at least 540°. The interval $I_{BP}(x)$ may be divided up, i.e. areas of the helical trajectory, in which the radiation source is visible from a location x, may be alternated with areas in which the radiation source is not visible from the location x. It is important that all the areas in which the radiation source is visible together cover an angle of greater than or equal to 540°. Acquisition in which the table feed is selected in this manner is known as 3-PI-acquisition. If, for example, the acquisition geometry is characterized by a fan angle of 52.1°, extension of the detector in the z-direction of 175.1 mm, a distance between the radiation source and the axis of rotation of 570 mm and a distance between the radiation source and the detector center of 1040 mm, a pitch of 57.6 mm may be selected, in order to allow 3-PI-acquisition. In other embodiments a different pitch would also be possible.

In step 105 the measured values are derived in accordance with equation (25) partially according to q, i.e. according to the angular position of the radiation source. It should be noted in this case that only y depends on q and not $\Theta$, such that, for derivation, in each case measured values of parallel rays must be taken into account. Since parallel rays comprise the same cone angle, in the case of the focus-centered detector 16 used here, as illustrated in FIG. 5, the parallel rays 51 hit the same detector row 53. In this case, the cone angle of a ray is the angle which this ray forms with a plane perpendicular to the axis of rotation. For partial derivation, the measured values may initially be resorted. To this end, measured values which belong to parallel rays 51, i.e. to the same detector row 53 but to different angular positions $s_a$, $s_b$, $s_c$ of the radiation source, are in each case combined into one quantity. The measured values of each quantity are derived for example numerically, using the known finite element method, according to the angular position of the radiation source, wherein smoothing methods may be used.

In step 107, the derived measured values are projected along their rays onto a notional, planar detector 60 (see FIG. 6). The planar detector 60 is rectangular and contains the axis of rotation 14. It is delimited by rays 62, 64, 66, 68, which radiate from the radiation source and hit the corners of the real, focus-centered detector 16.

In step 109, filter lines and filter directions are determined, wherein the filter lines indicate, together with the filter directions, in which sequence the measured values are filtered, i.e. in which sequence integration is performed over the κ-angle γ in equation (25). To this end, it will initially be explained what relationship exists between the filter lines or the filter directions and the κ-vectors $e_k(s,x)$.

Together with the vector $\beta(s,x)$, each κ-vector $e_k(s,x)$ generates a κ-plane. A change in the κ-angle γ then results, in accordance with equation (26), in a change in radiation direction $\Theta_k(s,x,\gamma)$ within the κ-plane. In the case of γ-integration, therefore, the measured values are processed for a given angular position s, a given location x and a vector $e_k(s,x)$ on the detector in the sequence in which the rays corresponding to the measured values vary with the directions $\Theta_k(s,x,\gamma)$ in the case of a varying γ, i.e. the measured values are filtered along the line of intersection between the detector surface and the κ-plane, which is defined in the case of the given s and x by a vector $e_k(s,x)$.

This is illustrated by way of example in FIG. 7. For a location x in the examination area and an angular position s or radiation source position y(s), the vector $\beta(s,x)$ 73 and a κ-vector $e_k(s,x)$ 72 are shown. The vectors $\beta(s,x)$ and $e_k(s,x)$ generate a κ-plane 70, which intersects the detector 74 in a line of intersection 76. The detector 74 is delimited by two successive turns of the helical trajectory 17 and exhibits the curvature of the helix 17. This detector was used here as an example for illustrative purposes. For other detectors, such as the focus-centered or the planar detector, corresponding lines of intersection 76 may be determined. The measured values which lie on the line of intersection 76 are filtered by row. A vector $e_k(s,x)$ thus defines a filter line 76, in the case of the given radiation source position s and the given location x in the examination area. An important factor for implementation of the method according to the invention is then not the κ-vectors $e_k(s,x)$, but rather the filter lines resulting from the κ-vectors.

As already described above, the κ-vectors $e_k(s,x)$ are selected in such a way according to the invention that equation (24) is fulfilled for all or at least a majority of possible combinations of vectors $I_{BP}(x)$ and locations ω in the examination area in the case of the given interval x. If equation (24) is fulfilled for all these combinations, equation (18) applies exactly, even after σ(x, ω) has been replaced by $\tilde{\sigma}/N(x)$. Therefore, back-projection according to equation (25) is in this case designated "exact". If equation (24) is only fulfilled for a majority of the combinations, the filtered back-projection according to equation (25) is designated "quasi-exact" for the purposes of the invention.

Each quantity of filter lines, which may be derived from κ-vectors $e_k(s_j,x)$ which fulfill equation (24) exactly or quasi-exactly, may be applied according to the invention.

The individual steps, which have led in this example of embodiment to κ-vectors $e_k(s_j,x)$ which fulfill equation (24) quasi-exactly, are described below and are illustrated in FIG. 8.

First of all, in step 200 values for $\tilde{\sigma}$ and $n_e$ are specified. Experiments with different values for $\tilde{\sigma}$ and $n_e$ have shown that, in the case of the 3-PI-acquisition used here, reconstruction may be performed for $\tilde{\sigma}=3$ and $n_e=3$ with relatively low computing power. These values are therefore selected for determining the κ-vectors. However, other values could also be specified for $\tilde{\sigma}$ and $n_e$. For each location x to be reconstructed, it would also be possible in each case to specify a value for $n_e$.

In step 202, an interval $I_{BP}(X)$ is determined for each location x to be reconstructed in the examination area. This may take place for example numerically by simulating acquisition, in particular the movement of the radiation source S on the helical trajectory 17.

In step 204, a location x in the examination area and in step 206 a vector ω are selected from a preset quantity of vectors ω. A preferred quantity of vectors ω, from which a vector is selected, may be formed as follows. First of all, planes are defined which are distributed uniformly in space and which all contain the location x selected in step 204. 100 to 1000 of these planes are preferably defined. The quantity of vectors ω is then formed by those vectors which extend normally to the respective plane and point from the origin of a reference coordinate system to the respective plane. The reference coordinate system may be a Cartesian system of coordinates, whose origin is for example a point on the axis of rotation 14.

Next, in step 208 all the angular positions $s_j$ within the interval $I_{BP}(x)$ or all the radiation source positions $y(s_j)$ for which equation (20) is fulfilled are calculated for the selected location x in the examination area and the selected vector ω. The angular positions $s_j$ are thus selected in such a way that the line connecting the radiation source $y(s_j)$ to the location x is oriented perpendicularly to the vector ω.

In step 210, the derivative $\dot{y}(s_j)$ is determined at the angular positions $s_j$ which were determined in step 208, and the values for x, ω and $\dot{y}(s_j)$ are inserted into equation (23). Since in step 200 $\tilde{\sigma}=3$ was selected, equation (23) represents a conditional equation for vectors $e_1(s_j, x)$, $e_2(s_j,x)$ and $e_3(s_j,x)$.

In step 214 it is checked whether all the vectors ω of the given quantity have already been used to determine the conditional equations in step 210. If this is the case, it is possible to continue with step 216. Otherwise, step 206 follows.

Whether all the locations x in the examination area have already been used to determine the conditional equations is investigated in step 216. If this is the case, step 218 follows. Otherwise, step 204 is performed.

In step 218, the system of conditional equations determined in step 210 is solved numerically, such that the vectors $e_1(s,x)$, $e_2(s,x)$ and $e_3(s,x)$ fulfill the equation $\tilde{\sigma}(x,\omega)=3$ at least for a majority of the combinations of vectors ω and locations x.

This method just described for determining a quantity of κ-vectors $e_k(s,x)$ should be understood solely as an example of embodiment. According to the invention, any method of determining κ-vectors may be applied which makes it possible, for a given type of acquisition, i.e. for example for a given pitch, to determine κ-vectors $e_k(s,x)$ which fulfill the equation (24) at least for a majority of combinations of the vectors ω and the locations x in the examination area.

Next, filter lines are determined by means of the vectors $e_k(s,x)$. To this end, for each angular position s of the radiation source and for each location x in the examination area, the vector $\beta(s,x)$ according to equation (5) is formed, which points from the radiation source to the location x. A κ-plane is then determined which is generated by the vectors $e_k(s,x)$ and β. A κ-plane is thus determined for each combination of radiation source position and location in the examination area, i.e. for each measured value, and for each vector $e_k(s,x)$. The lines of intersection between these κ-planes and the detector form the filter lines. At least one filter line is thus assigned to each measured value.

To determine the filter direction of a filter line of a measured value, an investigation is performed using equation (26) as to the direction in which the direction vector $\Theta_k(s,x,\gamma)$ moves on the filter line as the κ-angle γ grows. The direction of movement of the vector $\Theta_k(s,x,\gamma)$ for a given filter line is the filter direction.

Examples of results of this numerical determination of filter lines and filter directions are shown in FIGS. 9 to 13 and are explained below.

To this end, the planar detector is firstly divided into a plurality of areas. The area 92 is designated the PI-window and is delimited by two PI-lines 80 and 84. The PI-lines 80 and 84 may be described mathematically by the following equations:

$$v_{Pi}(u_{Pi}) = +\frac{h}{2\pi}\left(1 + \left(\frac{u_{Pi}}{R}\right)^2\right)\left(n\frac{\pi}{2} - \arctan\frac{u_{Pi}}{R}\right) \quad (26)$$

$$v_{Pi}(u_{Pi}) = -\frac{h}{2\pi}\left(1 + \left(\frac{u_{Pi}}{R}\right)^2\right)\left(n\frac{\pi}{2} + \arctan\frac{u_{Pi}}{R}\right) \text{where } n = 1. \quad (27)$$

Figure 9:
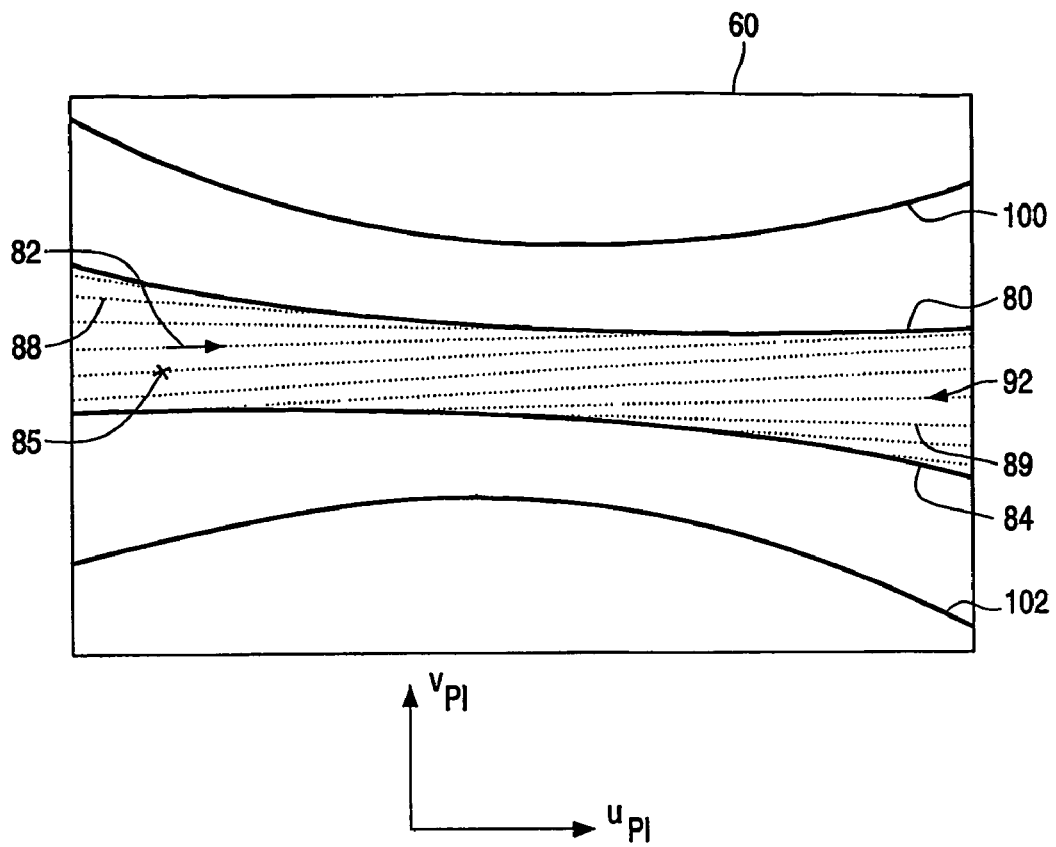

Here, $u_{P1}$ and $v_{P1}$ are coordinates on the planar detector 60 according to the system of coordinates in FIG. 9. This system of coordinates is illustrated, for reasons of clarity, beneath the planar detector 60. The origin of the system of coordinates is at the center of the detector, however. Furthermore, two 3-PI-lines 100 and 102 are introduced, which are described by the following equations:

$$v_{Pi}(u_{Pi}) = +\frac{h}{2\pi}\left(1 + \left(\frac{u_{Pi}}{R}\right)^2\right)\left(n\frac{\pi}{2} - \arctan\frac{u_{Pi}}{R}\right) \quad (28)$$

$$v_{Pi}(u_{Pi}) = -\frac{h}{2\pi}\left(1 + \left(\frac{u_{Pi}}{R}\right)^2\right)\left(n\frac{\pi}{2} + \arctan\frac{u_{Pi}}{R}\right) \text{where } n = 3. \quad (29)$$

The area of the detector enclosed by the two 3-PI-lines 100, 102 is known as the 3-PI-window.

In each case, three filter lines are assigned to each measured value located in the PI-window.

The first filter lines for measured values which lie in the PI-window were determined from the κ-vectors $e_1(s,x)$. A portion of these filter lines is illustrated in FIG. 9 in each case on the planar detector 60 and extends either tangentially to the PI-line 80 (filter lines 88, shown as dashed lines) or tangentially to the PI-line 84 (filter lines 89, shown as dotted lines). The portions of the filter lines 88 are in each case the portions of the tangents to the PI-line 80 which extend leftwards in FIG. 9 starting from the contact point. On the other hand, the portions of the filter lines 89 are the portions of the tangents to the PI-line 84 which extend to the right in FIG. 9 starting from the contact point. The portions of the filter lines 88 could also extend leftwards starting from the contact point, and the portions of the filter lines 89 could also extend to the right starting from the contact point. The only important factor here is that the portions of the filter lines 88, 89 extend in opposite directions starting from their respective contact point. The PI-window in FIG. 9 may be divided into two areas. One area is covered by the illustrated part of the filter lines 88 and the other area is covered by the illustrated part of the filter lines 89. The boundary between these areas is the line which extends asymptotically to the PI-lines 80, 84 from the left-hand end of the PI-line 80, in FIG. 9, to the right-hand end of the PI-line 84. Depending on the area on the detector 60 in which a measured value to be filtered is located, the corresponding filter line is assigned to the measured value. If a measured value is located for example at a point 85 on the detector 60, the first filter line 88 which contacts this measured value is assigned to said measured value. The filter direction along a filter line 88, 89 corresponds in this example of embodiment to the direction 82, i.e. from left to right in FIG. 9. In another embodiment, the direction 82 could also be oriented in the opposite direction.

Although the filter lines 88, 89 are not illustrated as extending over the entire detector, in the following step 111 filtering along a filter line is naturally carried out over the entire detector. This illustration was selected to make it clear that none of the filter lines 89 are assigned to measured values which lie in an area covered in FIG. 9 for example by the filter lines 88. If the filter lines 88, 89 had been drawn in in full, there would be areas on the detector in FIG. 9 in which both filter lines 88 and filter lines 89 would be present. This would be unclear. The same applies to FIGS. 10 and 13.

Figure 10:
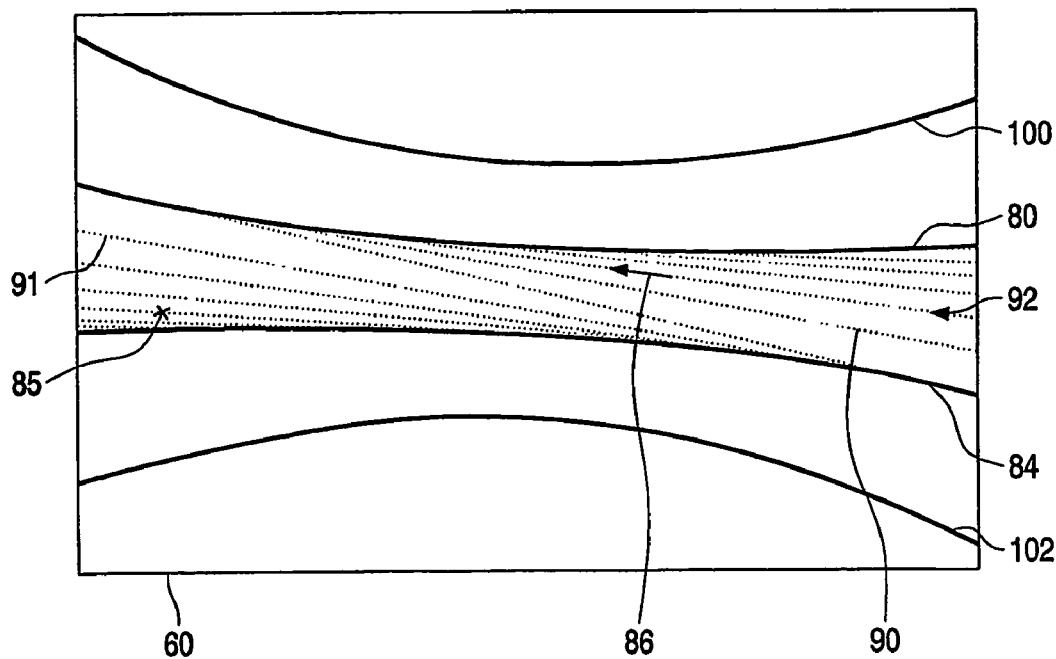

The second filter lines for measured values which lie in the PI-window were determined from the κ-vectors $e_2(s,x)$. Portions of these filter lines are illustrated in FIG. 10 on the planar detector 60 and also extend either tangentially to the PI-line 80 (filter lines 90, shown as dashed lines) or tangentially to the PI-line 84 (filter lines 91, shown as dotted lines). The portions of the filter lines 90 are the portions of the tangents to the PI-line 80 which, starting from the respective contact point, extend in the opposite direction from the portions of the filter lines 88 illustrated in FIG. 9. Likewise, the portions of the filter lines 91 are the portions of the tangents to the PI-line 84 which, starting from the respective contact point, extend in the opposite direction from the filter lines 89. In FIG. 10, the detector surface is again divided into two areas. One area is covered by the portions of the filter lines 90 and another area is covered by the portions of the filter lines 91. The boundary between these two areas forms the line which extends tangentially to the two PI-lines 80, 84 from the left-hand end of the PI-line 80, in FIG. 10, to the right-hand end of the PI-line 84. Depending on the area on the detector 60 in which a measured value to be filtered is located, the corresponding filter line is assigned to the measured value. Thus, for example, assigned to a measured value at the point 85 on the detector 60 is that second filter line 91 which contacts said measured value. The filter direction 86 is oriented substantially in the opposite direction from the filter direction 82 of the first filter line. Thus, in FIG. 10 it extends from right to left.

Figure 11:
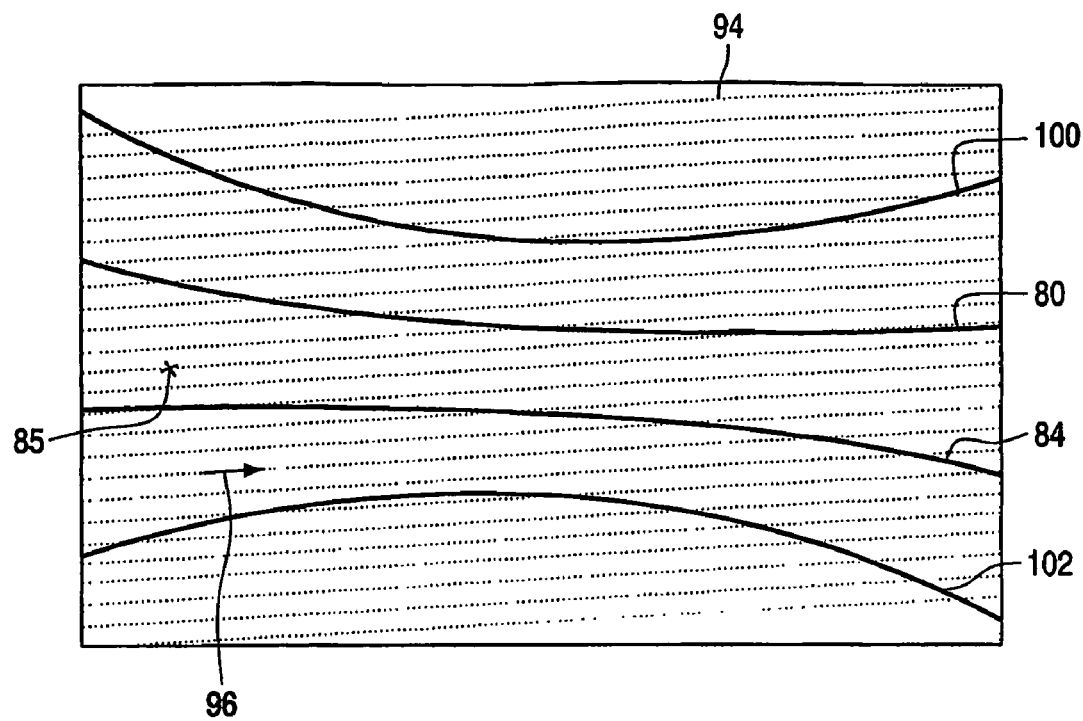

The third filter lines 94, for measured values which lie in the PI-window 92, were determined from the κ-vectors $e_3(s,x)$ and extend parallel to the projection of the vector $\dot{y}$ onto the planar detector 60. They thus extend in direction 96 of the derivative of the radiation source position y(s) on the helical trajectory according to the angular position s projected onto the planar detector 60. These filter lines 94 and the associated filter direction 96 are shown in FIG. 11.

Measured values which do not lie in the PI-window, but lie in the 3-PI-window, are filtered only along the filter lines 94 in the filter direction 96, i.e. one filter line 94 is assigned in each case to each of these measured values. Therefore, the filter lines 94 are also shown in the 3-PI-window in FIG. 11. In contrast to FIGS. 9 and 10, the filter lines in FIG. 11 run over the entire detector.

It is known from "The n-PI-Method for Helical Cone-Beam CT", IEEE Transactions on Medical Imaging, vol. 19, no. 9, pp. 848–863, 2000, that measured values during whose acquisition the radiation source was not located in the interval $I_{BP}(X)$ lie outside the 3-PI-window in the 3-PI-geometry. These measured values are not taken into account in back-projection, i.e. integration via the angular position s in equation (25). Therefore, no filter lines were determined for these measured values.

Figure 12:
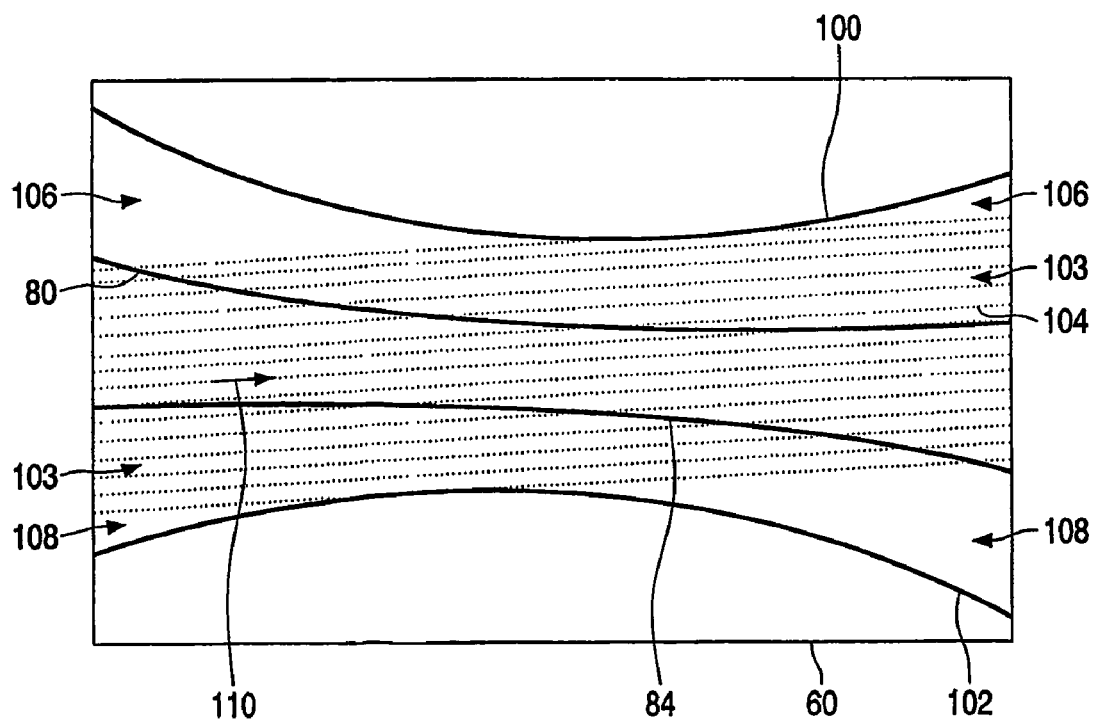

In another example of a result, the filter lines for measured values which lie in the PI-window extend unchanged. However, the filter lines do change for measured values which do not lie in the PI-window but do lie in the 3-PI window. This area known as the outer 3-PI window is in turn divided into a plurality of areas. An area 103 is formed by a quantity of parallels to ẏ, wherein all the parallels lie entirely in the 3-PI-window (see FIG. 12). Filter lines 104, which point in the direction 110 of the projection of ẏ onto the planar detector 60, are assigned to a measured value which lies in the outer 3-PI-window in an area 103, covered by the parallels. In FIG. 12, these filter lines are again shown over the entire detector. However, they are only assigned to measured values which lie in the area 103.

Figure 13:
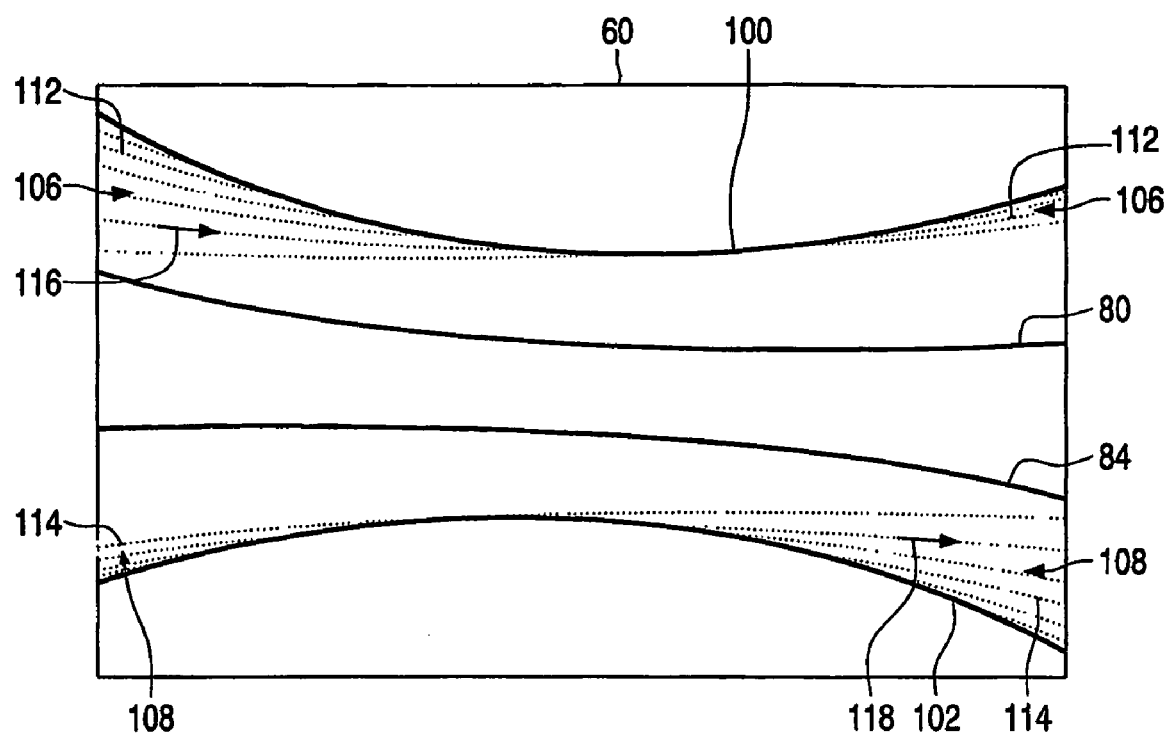

Measured values which lie in areas 106 not filled by the filter lines 104 within the outer 3-PI-window are assigned to filter lines 112 which extend tangentially to the 3-PI-line 100. In this case, assigned as filter line 112 to a measured value is that tangent which extends through this measured value and whose contact point is nearer to the center of the detector than the measured value itself. For measured values which lie within the 3-PI-window in areas 108, in this example filter lines 114 have been determined which extend tangentially to the 3-PI-line 102, wherein that tangent is assigned as filter line 114 to a measured value which extends through this measured value and whose contact point lies nearer to the center of the detector than the measured value itself. Filter lines 112 and 114 and their filter directions 116 and 118 are illustrated in FIG. 13.

The filter lines and filter directions presented should be understood merely as examples. According to the invention, all the filter lines and filter directions are applicable whose κ-vectors fulfill equation (24) at least for a majority of combinations of x and ω.

If the filter lines and directions have been determined for a particular type of acquisition, thus for example for 3-PI-acquisition, they may be used for all following reconstructions of measured values which have been acquired in this manner. If therefore these filter lines and directions are known, step 109 may be dispensed with.

Next, the measured values projected onto the planar detector 60 are filtered in step 111 along the filter lines determined in step 109, in accordance with equation (25).

To this end, first of all a measured value and a filter line associated with the measured value are selected. Along this filter line, the measured values are each multiplied in the filter direction with a weighting factor and summed. The weighting factor decreases as the sine of the κ-angle increases. It is in particular equal to the reciprocal of the sine of the κ-angle. The summation result is the filtered measured value. This is repeated for all the filter lines of this measured value, such that for one measured value a number of filtered measured values is determined which is equal to the number of filter lines. These filtered measured values are added up to yield one measured value. Then, another, as yet unfiltered measured value is selected and filtering is repeated along the filter lines of this measured value. If all the measured values have been filtered, filtering is complete.

To determine the filtered measured values on a filter line, the measured values are preferably reinterpolated on the planar detector 60 in such a way that they lie on this filter line equidistantly relative to the κ-angle. Then, the interpolated measured values are multiplied with the weighting factor according to equation (25) along the filter line and integrated, wherein multiplication with a weighting factor and integration may be performed in known manner by means of a Fourier transform.

The measured values may be filtered as follows with the filter lines shown in FIGS. 9 to 13.

Each measured value lying in the PI-window is filtered three times, along the three filter lines assigned in step 109. For each unfiltered measured value there are then three filtered measured values, which are added up to yield one measured value.

Each measured value lying in the 3-PI-window is filtered once, along the filter line assigned in step 109.

Filtering was here performed on the planar detector. However, it may be performed on any desired detector. The measured values and the filter lines would then optionally have to be projected onto this detector. It is sensible, in particular, to filter the measured values on the focus-centered detector. The projection of the measured values onto the planar detector performed in step 107 could then be dispensed with and the lines of intersection between the respective κ-planes and the focus-centered detector would have to be determined to determine the filter lines in step 109.

The filtered measured values are then used to reconstruct the absorption distribution in the examination area by back-projection, in this example of embodiment according to equation (25).

To this end, in step 113 a voxel V(x) is determined within a predeterminable area (field of view—FOV) in the examination area. Then, in step 115, an angular position s is preset within the interval $I_{BP}(x)$. In step 117 it is checked whether a measured value is present for the angular position s whose ray extends through the center of the voxel V(x). If such a ray cannot be found, it is determined at what point a central ray would have hit the detector surface. The associated measured value is then calculated by interpolation of the measured values from adjacent rays. The measured value which may be assigned to the ray passing the voxel or the measured value obtained by interpolation is multiplied in step 119 with a weighting factor, which becomes smaller as the distance between the radiation source y(s) and the location x to be reconstructed increases. In this embodiment, this weighting factor is equal to $1/|x-y(s)|$ according to equation (25). In step 120, the weighted measured value is accumulated on the voxel V(x). In step 121, it is checked whether all the angular positions s in the interval $I_{BP}(x)$ have been observed. If this is not the case, the flow chart branches off to step 115. Otherwise, it is checked in step 123 whether all the voxels V(x) in the FOV have been passed through. If this is not the case, it is possible to continue with step 113. If, on the other hand, all the voxels V(x) in the FOV have been passed through, the absorption has been determined in the entire FOV and the reconstruction procedure is complete (step 125).

LIST OF REFERENCE CHARACTERS/NUMERALS

αmax Aperture angle
S Radiation source
sa, sb, sc Angular position of radiation source
x Location in examination area
IPI(x) Helix portion
1 Gantry
2, 5 Motor 3 Collimator arrangement
4 Beam
7 Control unit
10 Image processing computer
11 Monitor
13 Examination area
14 Axis of rotation
16 Detector unit
17 Trajectory
31 PI-boundary line
51 Parallel rays
53 Detector row
60 Planar detector
62, 64, 66 68 Beam rays
70 κ-Plane
72 κ-Vector
73 β-Vector
74 Detector
76 Line of intersection
80, 84 PI-line
82 Filter direction for filter lines 88, 89
85 Point on detector surface
86 Filter direction for filter lines 90, 91
88, 89, 90, 91 Filter lines for measured values in PI-window
92 PI-window
94 Filter lines for measured values located in 3-PI-window
96 Filter direction for filter line 94
100, 102 3-PI-lines
103, 106, 108 Detector area in outer 3-PI-window
104 Filter lines for measured values in detector area 103
110 Filter direction for filter lines 104
112 Filter lines for measured values in detector area 106
114 Filter lines for measured values in detector area 108
116 Filter direction for filter line 112
118 Filter direction for filter line 114

The invention claimed is:
1. A computerized tomography method having the steps:
a) generation with a radiation source of a conical beam passing through an examination area and an object located therein,
b) production of relative movement between the radiation source on the one hand and the examination area on the other, which comprises rotation about an axis of rotation and displacement parallel to the axis of rotation and takes the form of a helix, wherein the position of the radiation source on the helix is defined by an angular position,
c) acquisition of measured values with a detector unit during the relative moment, whereby the measured values depend on the intensity in the beam on the other side of the examination area and the detector unit comprises a detector surface,
d) reconstruction of a CT image of the examination area from the measured values, wherein an exact or quasi-exact, filtered 3D back-projection with redundant measured values is performed according to the following steps:
determination of the partial derivative of measured values from parallel rays with different radiation source positions depending on the angular position of the radiation source on the helix,
filtering of the derived measured values along filter lines, wherein a plurality of filter lines are assigned to at least some of the measured values, such that these measured values are filtered several times, reconstruction of the absorption distribution at locations to be reconstructed in the examination area by back-projection of the measured values.

2. A computerized tomography method as claimed in claim 1, wherein filtering of a derived measured value in each case comprises the following steps:
provision of a plurality of filter lines, wherein at least one filter line is assigned to each measured value and a filter direction is assigned to each filter line,
multiplication of measured values along each filter line assigned to the measured value with a weighting factor, which corresponds to the reciprocal of the sine of the κ-angle,
addition of all weighted measured values along each filter line of the measured value in the filter direction which has been assigned to the respective filter line, such that a sum is generated per filter line,
addition of the sums to yield a filtered measured value.

3. A computerized tomography method as claimed in claim 2, wherein the provision of a plurality of filter lines comprises the following steps:
determination of κ-vectors, which allow exact or quasi-exact reconstruction, wherein at least one κ-vector is assigned to each combination of radiation source position and location to be reconstructed in the examination area,
determination of in each case one κ-plane for each combination of radiation source position and location to be reconstructed in the examination area and each κ-vector assigned to the respective combination,
determination of in each case one line of intersection for each κ-plane between the respective κ-plane and the detector surface, wherein each line of intersection constitutes in each case a filter line,
determination of in each case one filter direction for each filter line and assignment of the respective filter direction to the corresponding filter line,
assignment of each filter line to a measured value which corresponds to the combination, associated with the filter line, of location to be reconstructed in the examination area and radiation source position.

4. A computerized tomography method as claimed in claim 1, wherein filtering of a derived measured value comprises the following steps in the case of 3-PI-acquisition:
if the measured value lies on the detector surface in a PI-window, assignment of three filter lines, to which in each case one filter direction is assigned, to the measured value,
if the measured value lies on the detector surface in the outer 3-PI-window, assignment of one filter line, to which a filter direction is assigned, to the measured value,
multiplication of measured values along each filter line assigned to the measured value with a weighting factor, which corresponds to the reciprocal of the sine of the κ-angle,
addition of all weighted measured values along each filter line of the measured value in the filter direction which has been assigned to the respective filter line, such that a sum is generated per filter line.

5. A computerized tomography method as claimed in claim 1, wherein filtering of a derived measured value comprises the following steps in the case of 3-PI-acquisition:
if the measured value lies on the detector surface in a PI-window, assignment of three filter lines, to which in each case one filter direction is assigned, to the measured value, wherein a first filter line extends tangentially to a first PI-line, a second filter line extends tangentially to a second PI-line and a third filter line extends parallel to the derivative of the radiation source position in accordance with the angular position thereof projected onto the detector surface, if the measured value lies on the detector surface in the outer 3-PI-window, assignment to the measured value of one filter line, to which a filter direction is assigned which extends parallel to the derivative of the radiation source position in accordance with the angular position thereof projected onto the detector surface, multiplication of measured values along each filter line assigned to the measured value with a weighting factor, which corresponds to the reciprocal of the sine of the κ-angle, addition of all weighted measured values along each filter line of the measured value in the filter direction which has been assigned to the respective filter line, such that a sum is generated per filter line, addition of the sums to yield a filtered measured value.

6. A computerized tomography method as claimed in claim 1, wherein filtering of a derived measured value comprises the following steps in the case of 3-PI-acquisition:

if the measured value lies on the detector surface in a PI-window, assignment of three filter lines, to which in each case one filter direction is assigned, to the measured value, wherein a first filter line extends tangentially to a first PI-line, a second filter line extends tangentially to a second PI-line and a third filter line extends parallel to the derivative of the radiation source position in accordance with the angular position thereof projected onto the detector surface, if the measured value lies on the detector surface in the outer 3-PI-window and in an area which is covered by lines which extend parallel to the derivative of the radiation source position in accordance with the angular position thereof projected onto the detector surface and wholly within the 3-PI-window, assignment of one filter line to which a filter direction is assigned and which extends parallel to the lines, if the measured value lies on the detector surface in the outer 3-PI-window and in an area which is delimited by the lines and a 3-PI-line, assignment of one filter line, to which a filter direction is assigned and which extends tangentially to the delimiting 3-PI-line, multiplication of measured values along each filter line assigned to the measured value with a weighting factor, which corresponds to the reciprocal of the sine of the κ-angle, addition of all weighted measured values along each filter line of the measured value in the filter direction which has been assigned to the respective filter line, such that a sum is generated per filter line, addition of the sums to yield a filtered measured value.

7. A computerized tomography method as claimed in claim 1, wherein, in step d) during back-projection of the measured values, each measured value is multiplied with a weighting factor which diminishes as the distance between the location to be reconstructed in the examination area and the radiation source increases.

8. A computer tomograph, in particular for performing the method as claimed in claim 1 with
 a radiation source for generating a conical beam passing through an examination area or an object located therein,
 a drive arrangement to allow rotation of an object contained in the examination area and the radiation source relative to one another about an axis of rotation and displacement parallel to the axis of rotation,
 a detector unit, coupled to the radiation source and comprising a detector surface, for the acquisition of measured values,
 a reconstruction unit for reconstruction of the absorption distribution within the examination area from the measured values acquired by the detector unit,
 a control unit for control of the radiation source, the detector unit the drive arrangement and the reconstruction unit in accordance with the following steps:
  a) generation with a radiation source of a conical beam passing through an examination area and an object located therein,
  b) production of relative movement between the radiation source on the one hand and the examination area on the other, which comprises rotation about an axis of rotation and displacement parallel to the axis of rotation and takes the form of a helix, wherein the position of the radiation source on the helix is defined by an angular position,
  c) acquisition of measured values with a detector unit during the relative moment, whereby the measured values depend on the intensity in the beam on the other side of the examination area and the detector unit comprises a detector surface,
  d) reconstruction of a CT image of the examination area from the measured values, wherein an exact or quasi-exact, filtered 3D back-projection with redundant measured values is performed according to the following steps:
 determination of the partial derivative of measured values from parallel rays with different radiation source positions depending on the angular position of the radiation source on the helix,
 filtering of the derived measured values along filter lines, wherein a plurality of filter lines are assigned to at least some of the measured values, such that these measured values are filtered several times,
 reconstruction of the absorption distribution at locations to be reconstructed in the examination area by back-projection of the measured values.

9. A computer readable medium including a computer program for a control unit for controlling a radiation source, an aperture arrangement, a detector unit, a drive arrangement and a reconstruction unit of a computer tomograph for performing the method as claimed in claim 1 according to the following sequence:
 a) generation with a radiation source of a conical beam passing through an examination area and an object located therein,
 b) production of relative movement between the radiation source on the one hand and the examination area on the other, which comprises rotation about an axis of rotation and displacement parallel to the axis of rotation and takes the form of a helix, wherein the position of the radiation source (S) on the helix is defined by an angular position,
 c) acquisition of measured values with a detector unit during the relative moment, whereby the measured values depend on the intensity in the beam on the other side of the examination area and the detector unit comprises a detector surface, d) reconstruction of a CT image of the examination area from the measured values, wherein an exact or quasi-exact, filtered 3D back-projection with redundant measured values is performed according to the following steps:

determination of the partial derivative of measured values from parallel rays with different radiation source positions depending on the angular position of the radiation source on the helix, filtering of the derived measured values along filter lines, wherein a plurality of filter lines are assigned to at least some of the measured values, such that these measured values are filtered several times, reconstruction of the absorption distribution at locations to be reconstructed in the examination area by back-projection of the measured values.

* * * * *